United States Patent [19]
Hamel et al.

[11] Patent Number: 6,116,452
[45] Date of Patent: Sep. 12, 2000

[54] METHOD AND APPARATUS FOR COMBINING THE LID-SECURING AND CARRYING FUNCTIONS OF COVERED CONTAINERS

[75] Inventors: Ross Jonathan Hamel; Michael Norman Langmaid, both of West Chester, Pa.

[73] Assignee: Synthes, Paoli, Pa.

[21] Appl. No.: 09/343,498

[22] Filed: Jun. 30, 1999

[51] Int. Cl.[7] .............................. B65D 45/04; B65D 43/12
[52] U.S. Cl. .......................... 220/318; 220/324; 220/322; 220/756; 220/345.2; 220/345.4; 220/351; 206/439; 206/370
[58] Field of Search ...................... 220/293, 297, 220/345.1, 345.2, 351, 345.4, 318, 322, 324, 755, 756, 764, 766, 770, 772; 206/438, 439, 370, 363; 422/297, 300, 292

[56] References Cited

U.S. PATENT DOCUMENTS

| | | | |
|---|---|---|---|
| 590,793 | 9/1897 | Rehfuss | 215/286 |
| 1,861,768 | 6/1932 | Wappler . | |
| 2,272,538 | 2/1942 | Wirth | 220/322 |
| 2,741,398 | 4/1956 | Riener | 220/766 |
| 3,024,940 | 3/1962 | Meyer | 220/324 |
| 3,273,747 | 9/1966 | Kalz | 220/766 |
| 4,267,939 | 5/1981 | Perrett et al. | 220/318 |
| 4,617,178 | 10/1986 | Nichols . | |
| 4,643,303 | 2/1987 | Arp et al. | 206/370 |
| 4,728,504 | 3/1988 | Nichols | 422/297 |
| 4,752,453 | 6/1988 | Nichols | 422/300 |
| 4,798,292 | 1/1989 | Hauze | 206/439 |
| 4,915,913 | 4/1990 | Williams et al. . | |
| 4,915,918 | 4/1990 | Nichols | 422/292 |
| 5,080,874 | 1/1992 | Nichols | 422/300 |
| 5,125,697 | 6/1992 | Kahl et al. | 220/324 |
| 5,129,538 | 7/1992 | Bennett | 220/345.1 |
| 5,183,643 | 2/1993 | Nichols | 422/297 |
| 5,207,325 | 5/1993 | Kennedy | 206/370 |
| 5,211,915 | 5/1993 | Monch . | |
| 5,279,800 | 1/1994 | Berry, Jr. | 422/300 |
| 5,346,075 | 9/1994 | Nichols et al. . | |
| 5,384,103 | 1/1995 | Miller . | |
| 5,415,846 | 5/1995 | Berry, Jr. | 422/297 |
| 5,424,048 | 6/1995 | Riley | 422/300 |
| 5,441,707 | 8/1995 | Lewis et al. | 422/300 |
| 5,525,314 | 6/1996 | Hurson | 422/300 |
| 5,573,741 | 11/1996 | Riley | 422/300 |
| 5,628,970 | 5/1997 | Basile et al. | 422/297 |
| 5,904,269 | 5/1999 | Wolff | 220/756 |
| 5,992,671 | 11/1999 | Wardani | 220/293 |

FOREIGN PATENT DOCUMENTS

WO 97/30737  8/1997  WIPO .

*Primary Examiner*—Nathan J. Newhouse
*Attorney, Agent, or Firm*—Pennie & Edmonds LLP

[57] ABSTRACT

The present invention provides an improved system and method for carrying and securing the lid of a container, such as a surgical sterilization tray. A tray is provided with rotating wire bail handles and at least two studs. The cover for the tray has a keyway and cutout which can be engaged with the studs when the lid is placed onto the case. Inadvertent disengagement of the keyway or cutout from the studs is prevented by the interaction of the handles with the lid. The lid is provided with slots and end panels which become mechanically associated with the handles when the handles are rotated to any of a variety of lid-securing positions. The association of the handles with the lid prevents any relative sliding motion of the lid and case which would allow disengagement of the keyway or cutout and the studs, until the handles are rotated to any of a variety of non-lid-securing positions. The system combines the handle and lid-securing functions in a very low part-count design with very few moving parts. The system can be grasped and lifted even when the tray can only be accessed from above, offers improved ergonomics over known systems, can be grasped using full-hand grip of the handles, and may be grasped and lifted using one hand. Even when the system is carried by one hand and is suspended sideways, the lid remains positively secured to the case.

17 Claims, 4 Drawing Sheets

METHOD AND APPARATUS FOR COMBINING THE LID-SECURING AND CARRYING FUNCTIONS OF COVERED CONTAINERS

TECHNICAL FIELD

The present invention relates to container systems, and, more particularly, to an improved system for securing the lid of a container to the body of a medical case and for carrying the case.

BACKGROUND OF THE INVENTION

It is necessary in hospitals and other medical environments to organize medical implants and surgical instrumentation in surgical cases. The implants and instruments are typically held in various brackets and trays within the case, so as to be presented in a convenient, organized fashion upon their use in a medical procedure, such as a surgical procedure. These surgical cases are typically provided with a lid to protect the contents.

The demands on medical personnel involved in surgical procedures are often very great. For example, many procedures may be performed in the context of trauma treatment, requiring prompt treatment of an injured patient. Even in the context of the scheduled treatment of a patient, unexpected developments during the course of the procedure can create great urgency. Accordingly, medical personnel are often operating under substantial time constraints and a great deal of resultant psychological pressure, based on the stakes involved in the proper performance of their duties (the health, or possibly even the life, of the patient). It is not an exaggeration to state that the delay of even a few seconds can cost a life in emergency treatment. Therefore, it is critical that the apparatus and methods used by such personnel are designed to work as efficiently and safely as possible, in order to allow the personnel to perform their work quickly, as well as to accommodate minor mistakes and mishaps which may occur in the course of such high-pressure work.

In the context of surgical cases, a case must offer a convenient hand-hold so that it can be quickly grasped and lifted. The hand-hold may be a handle protruding from the case body, an opening in the case walls for the fingertips to be inserted, a protrusion on the case walls for fingertip gripping, or in some cases may simply be the flat outer side walls of the case itself.

Ideally, the hand-hold will allow the case to be grasped and lifted by one hand. This will allow medical personnel who are already using one hand to carry something else, to grasp and lift the case. Also, a case which is designed to be carried by one hand should accommodate the situation where it is grasped and lifted by both hands, and then one hand loses its grip. It is also preferable that at least when not in use, the hand-hold will not protrude too far from the walls of the case.

It is also common for surgical trays to be presented in situations where physical access to the tray is limited. For example, trays may often be stored in such a way that lateral access to the ends or side of the tray is not available. Furthermore, surgical trays may be disposed in use in sterilization enclosures which also limit lateral access to the tray. In such situations, grasping and lifting of prior art trays, in which the handles are projections on the end walls of the base or around the edges of the top of the lid, will be difficult if not impossible. Accordingly, there is a need in the art for a system which provides a handle system allowing convenient grasping and lifting of the surgical tray when the tray can only be accessed from above.

Prior art hand-hold systems for surgical cases do not typically meet all of these design criteria. For example, U.S. Pat. No. 4,728,504 to Nichols, entitled "Stackable Medical Instrument Sterilizer Container" discloses a container 10 including a housing 12 having handles 28 provided on opposite ends of the container to facilitate handling of the container. The handles 28 are arched protrusions which allow only a fingertip grip, which is weaker than a full hand grip. Also, these handles 28 do not permit the case to be securely carried by one hand. U.S. Pat. No. 5,415,846 to Berry, Jr., entitled "Plastic Autoclave Tray and Lid Combination" discloses an autoclave tray 21 having an outwardly extending flange 25 and is typical of prior art systems which have a simple rim around the edge of the case. The rim can be used for a fingertip hold, and has the same problems as discussed above with reference to the Nichols '504 patent. Handle systems such as those of the Berry and Nichols patents do not allow the tray to be lifted from above when the tray system is in a confined space such that only the top surface of system is accessible. Specifically, if those trays were in an enclosure open at the top and closely matching the outer periphery of the tray, they could not be grasped and lifted, as it would not be possible for the user's hands to grip the handles.

The lid of a surgical case must also be designed with both safety and ease of use in mind. A lid which is unduly cumbersome to remove will cause an unacceptable delay in accessing the products inside the case. On the other hand, if the lid comes off too easily, it may come off accidentally or prematurely, for example during transport. A loose lid that accidentally becomes separated from the case may allow the case contents to become disarranged or result in the spillage of the case contents, delaying the surgery and possibly resulting in damage to the case contents. Also, a loose lid may in itself present a hazard if it falls to the floor in a busy area.

Underlying all of the constraints discussed above are fundamental ergonomic design concepts which apply to any product which people use. A product should be a simple as possible while accomplishing the required function, with a minimum of moving parts, and its method of use should be simple and easily understood from the product itself. Furthermore, the product should be simple and inexpensive to manufacture. Thus, it is preferable that the hand-hold and lid-securing functions be combined, such that they are performed at least in part by the same structural elements of the case system. The simplicity of the mechanical design is particularly important in the surgical tray field, as complex designs having many mating parts will be more difficult to properly sterilize.

Systems combining the hand-hold and lid-securing functions are known in the art. For example, U.S. Pat. No. 4,915,913 to Williams et al., entitled "Medical Sterilizer Device with Improved Latch Mechanism" discloses a medical sterilization case 4 and a cover C which is latched to the body of case by a pair of latch mechanisms 20. Each latch mechanism includes a handle 22 and a complicated latch mechanism 20 which includes, among other components, a hinge plate 106, an elongated retention member 110, a second retention member 116, a latch plate 130, and coil springs 142. These components are arranged so as to provide a pivoting, double-action latching system for the cover C. The Williams system is unduly complex for the simple functions being performed. Also the handle 22 is provided as a means to accomplish the unlatching of the latch mechanism, and is not well adapted to be used to pick up the case. If used to pick up the case, the force applied to the handle 22 would tend to result in the inadvertent unlatching of the latch mechanism, undesirably allowing the cover to come free prematurely.

The Berry '846 patent, discussed above, also discloses a relatively complex latching mechanism. In Berry, a frame 50, a spring clip 51, a slide 52, collar 53, and cooperating screw stud 53a are assembled to form a slide latch assembly which allows the lid 22 to be releasably secured to the tray 21. Similarly, U.S. Pat. No. 5,384,103 to Miller, entitled "Instrument Tray," also discloses a complex locking mechanism 16 which is disposed on the outer surface of each of the tray end walls (see, for example, FIG. 4 of Miller and associated text at 6:54–7:42). Also, the handles of the Miller tray may be accessed through openings in the cover, but the system is not designed to take advantage of any mechanical association of the handles with the lid to contribute to securement of the lid. Although Miller is directed to the problem of providing a releasable locking system for a tray lid, as in the Williams and Berry patents, the locking mechanism 16 provided by Miller is an inordinately complex design solution for the problem addressed.

Accordingly, there is a need in the art for a combined surgical case handling and lid securing system having improved ergonomics and allowing a firm, secure full-hand grasp, and which permits one-handed grasping, lifting, and carrying of the case as well as positively engaging the lid to the case until its removal is desired. The handle of the lid is accessible even when the system is approachable only from the top. The lid should remain positively secured to the case even when the case is held sideways, for example when one hand is used to grasp, lift and carry the case. The hand-holding and lid-securing functions should be combined in a single system, such that parts serving one function also contribute to the other function. There is also a need in the art for a surgical case lid-securing system meeting these specifications that is simple and inexpensive to manufacture and is simple to use.

SUMMARY OF THE INVENTION

Accordingly, the invention addresses this need by providing a design which combines the lid-securing and carrying functions for a covered container system having improved ergonomics while allowing a firm, secure full-hand grasp, and which permits one-handed grasping, lifting, and carrying of the case as well as positively engaging the lid to the case until its removal is desired. The invention also provides a combined lid-securing and carrying system for a covered container in which the lid remains positively secured to the container even when the container is held sideways, for example when one hand is used to grasp, lift and carry the case. Furthermore, the invention provides a combined lid-securing and carrying system for a covered container in which the parts serving one of the lid-securing and carrying functions also contribute to the other function. In addition, the combined lid-securing and carrying system is simple and inexpensive to manufacture and is simple to use.

Thus, the invention relates to a covered tray system comprising a case and a lid. The case comprises a base, at least one wall, and a longitudinal axis parallel to the wall, each wall extending from the base and having a top edge which forms an opening for the case. A pair of rotatable handles are mounted to the wall, each handle having a rotation axis substantially perpendicular to the longitudinal axis, and a hand-grip portion. The handles are mounted in opposed relation and are rotatable, about the rotation axis, from a non-lid-securing position to at least one lid-securing position in which the hand-grip portion can be grasped using a full hand hold. First and second studs extending from the base toward the opening are also provided, with at least the first stud having a shaft and a head which is larger than the shaft. The lid covers the case opening, and includes a substantially planar portion having at least one keyway and at least one cutout. The keyway has a relatively smaller opening portion, a relatively larger opening portion, and a keyway axis substantially perpendicular to the longitudinal axis of the case. The keyway is operatively associated with the first stud with the smaller opening portion of the keyway being larger than the shaft but smaller than the head of the first stud, and the larger opening of the keyway being larger than the head of the first stud, while the cutout is operatively associated with the second stud. By this arrangement, movement of the lid in a direction transverse to the longitudinal axis is prevented when the handles are rotated to the lid-securing position, and the combination of the engagement of the at least one keyway with the first stud and the cutout with another stud results in a positive removable securement of the lid to the case, such that the lid cannot be removed until the handles are rotated to the non-lid-securing position in which they are completely disassociated from the lid and the lid is moved transversely relative to the case such that the at least one keyway can be disengaged from the first stud by lifting the lid away from the case.

The first and second studs are preferably positioned in opposed relation on an axis that is perpendicular to a line extending between the opposed handles. Generally, at least two opposite side walls and two opposite end walls are included, each wall being joined to the base such that the top edges of the walls form a substantially rectangular opening, with the handles located on the end walls and the studs located adjacent the side walls. Each handle preferably includes at least one link arm and the lid includes slots for receiving the link arms when the handles are rotated to the lid-securing position. Advantageously, at least two first and two second studs are provided, with each stud having a shaft and a head which is larger than the shaft, and wherein the lid includes two keyways for engaging the first studs and two cutouts for engaging the second studs.

In another embodiment, the invention relates to a tray system comprising a substantially rectangular case comprising a pair of opposite end walls, a pair of opposite side walls, a base, and a longitudinal axis parallel to the side walls. Each corner of the case opening is provided with upwardly-projecting studs. The studs have a substantially cylindrical shaft and a substantially cylindrical head, the head diameter being greater than the shaft diameter.

A rotatable handle is mounted to each of the end walls, in a hub provided for that purpose on the wall of the case. Each handle includes a hand-grip portion and a link arm. The handles may be wire bail handles, and may be formed from a single bent length of metal stock, or may be formed from two lengths of metal stock joined together, a first length forming the axle element, and the second length forming the gripping element.

The lid for the case includes a substantially planar portion having longitudinal slots arranged to accept the link arms of the handles when the handles are in certain lid-securing positions. The corners of the lid are provided with stud-engaging features corresponding to each stud on the case. The stud-engaging features may be keyways or topologically open cutouts. The lid may optionally include downwardly-depending end panels located at the ends of the lid. The end panels are disposed outside the end walls of the case when the lid is secured to the case.

The lid may be slid onto the case such that the keyways and/or cutouts engage with the studs to secure the lid to the case. When the handles are rotated into lid-securing positions such that they are associated with the lid, inadvertent sliding of the lid which could result in disengagement of the keyways and/or cutouts from the studs is prevented. Only when the handles are rotated to a non-lid-securing position, such that they are totally disassociated from the lid, may the lid be slid relative to the case such that the keyways and/or cutouts become disengaged from the studs.

The end panel of the lid may be shaped such that the combination of an end panel and the link arms of the corresponding handle constitutes a stop. The stop allows the lid to be moved transversely relative to the case, but prevents it from overshooting the position at which the keyways are disengaged from the stud such that the lid can be lifted away from the case directly upwards. The end panels may be provided with an embossed recess to facilitate handling of the lid.

If a plurality of cases are to be stacked, the base of the cases may optionally be provided with stacking features, such that the studs of a lower case will mechanically engage with the stacking features on the base of an upper case stacked on top of it, improving stability of stacked cases. The stacking features may be holes or recesses in the base of the case.

BRIEF DESCRIPTION OF THE DRAWINGS

The features and advantages of the present invention will become more readily apparent from the following detailed description of the invention in which like elements are labeled similarly and in which.

DETAILED DESCRIPTION OF THE PREFERRED EMBODIMENTS

The combined hand-hold and lid-securing system of the present invention is discussed herein with reference to a preferred embodiment adapted to be used in a transportation case for surgical implants and instruments. One of ordinary skill in the art will readily understand that the invention is not limited to rectangular surgical cases, but rather finds general application for use with any type or configuration i.e., round, oval, polygonal, etc., of covered container which is intended to be carried by hand.

Figure 1:
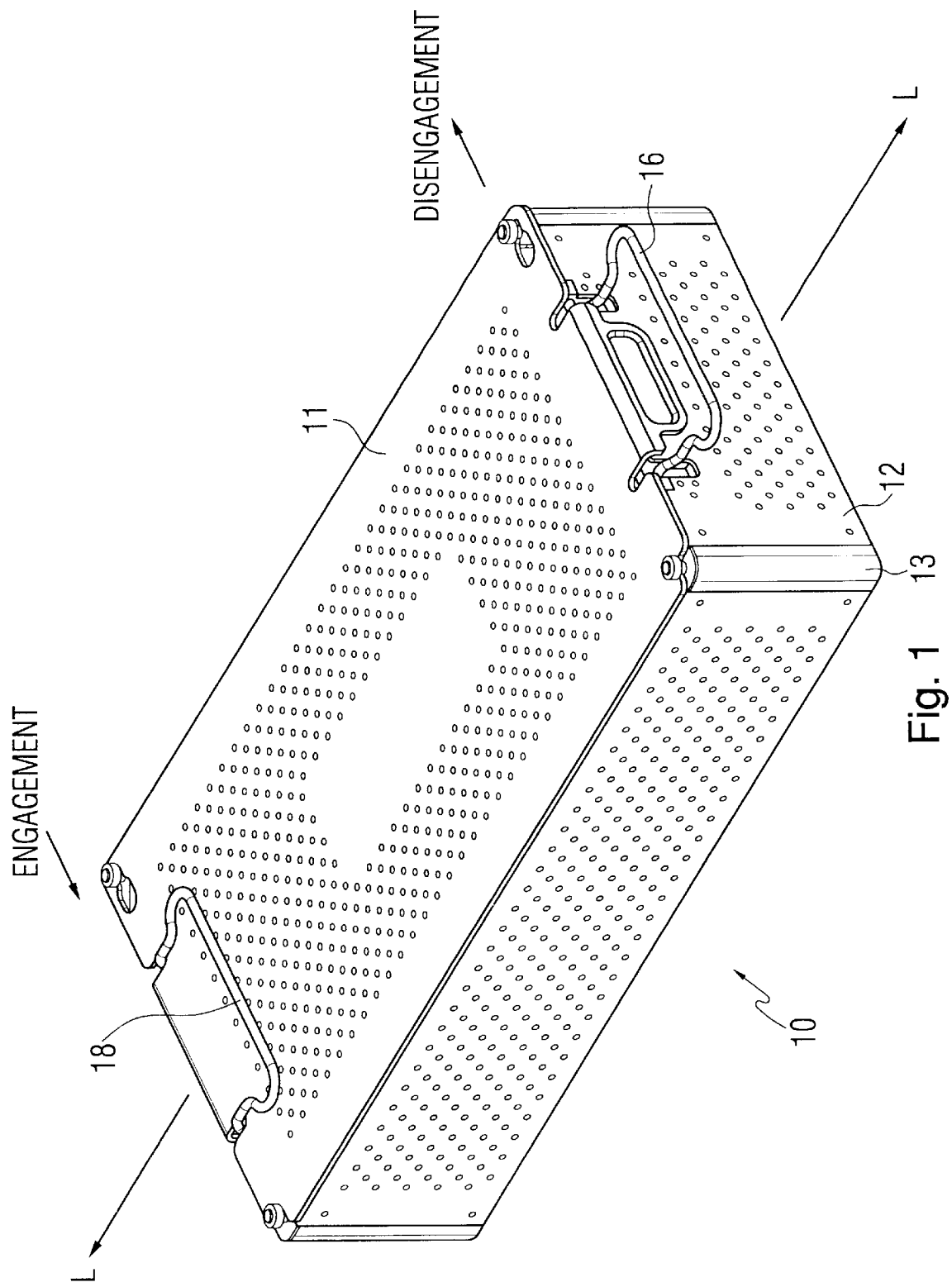
FIG. 1 is a perspective view of a system embodying the present invention, showing a lid secured to a case.
Figure 4:
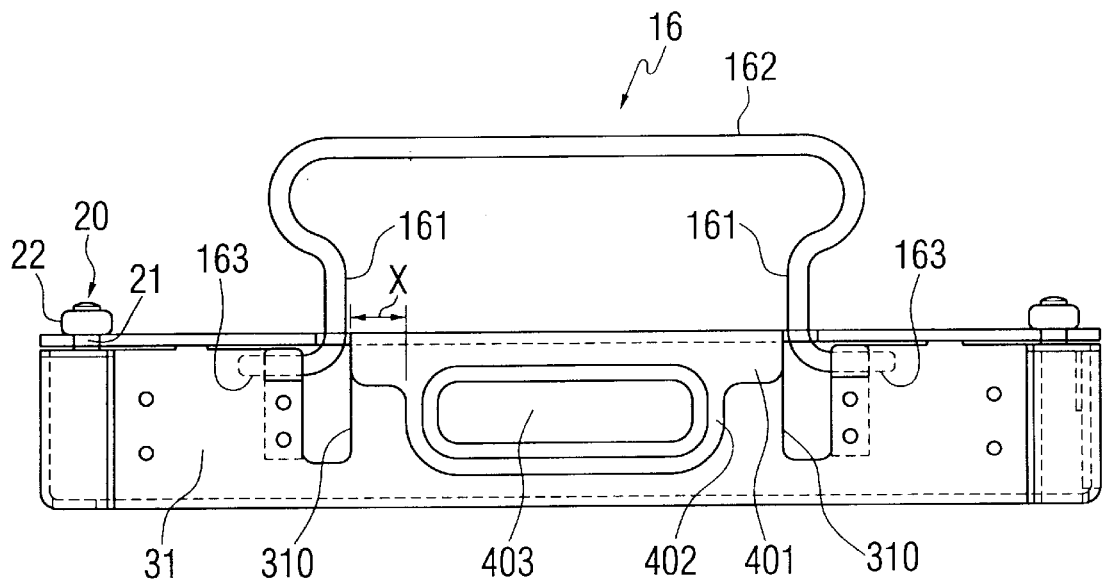
FIG. 4 is an end elevation view of a system embodying the present invention.

FIG. 1 is a perspective view of the preferred, rectangular, surgical tray system 10 of the present invention. It generally includes a lid 11 (also often referred to as a cover) and a case 12 (also often referred to as a tray). The case 12 (also shown in FIG. 2) is typically substantially rectangular in shape, with opposite end walls 31, 32, opposite side walls 33, 34, a floor or base 35, and a longitudinal axis L—L parallel to the side walls and perpendicular to the end walls. The term substantially is used to include designs in which the corners of the tray and lid are not perfectly rectangular but include rounded or other interruptions from a perfectly rectangular configuration. The end walls are provided with hubs 70, into which rotatable handles 16, 18 are mounted. The end walls are also provided with notches 310 (as best seen in FIG. 4) which are arranged to accept the link arms of the handles when the handles are rotated to certain positions.

The walls and base may be separate pieces which are joined together to form the case, or the case may be formed from a single piece of sheet material cut in the appropriate shape, and the walls folded perpendicular to the base to form a three-dimensional case. Regardless of what particular manufacturing method is used, it can be seen that each wall has two side edges, a top edge, and a bottom edge; for example, side wall 33 has two side edges 33S, a top edge 33T, and a bottom edge 33B. The three-dimensional case structure results from the bottom edge of each wall being joined to the periphery of the base. When the walls are provided as initially distinct pieces from the base, the joining requires an actual manufacturing step, whereas if the walls and base are formed from a unitary piece of material, the joining of the bottom edge of each wall to the base is simply a preexisting condition of the unitary formation. The top edges of the walls form a rectangular opening 36 at the top of the case.

The opening at the top of the case has four corners 38a–d. Upwardly projecting studs 20 are conveniently provided at one or more of the corners. It is only necessary to provide two studs, and these do not have to be in the corners by can be at any point along the sidewalls. In a preferred embodiment, studs will be provided at all four corners as shown in FIG 1. The studs are formed with a cylindrical shaft 21 and a cylindrical head 22. In order to properly interact with the keyways 60 and cutouts 65 provided on the lid (as described in detail below, with reference to FIG. 3A), the diameter of the head is greater than that of the shaft. Although the shaft and head are preferably cylindrical (i.e., having circular cross-section), other cross-sectional shapes such as oval or polygonal are contemplated and are also within the scope of the invention. The length of the shaft 21 is preferably slightly more than the thickness of the planar portion 41 of the lid.

Figure 3B:
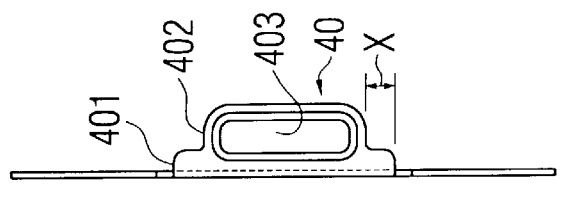
FIGS. 3A, 3B, and 3C are a top plan view, an end elevation view, and a side elevation view, respectively, of the lid of the system illustrated in FIG. 1.
Figure 3A:
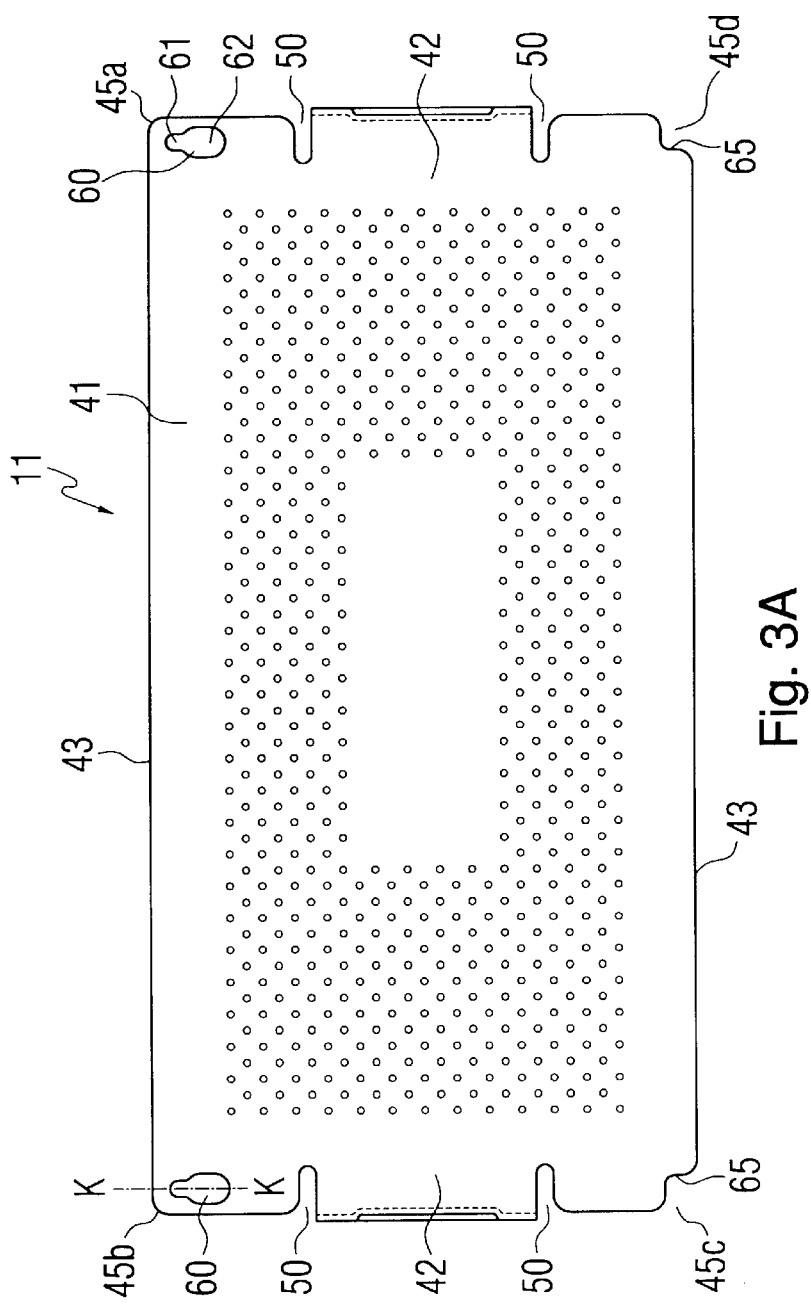
Figure 3C:
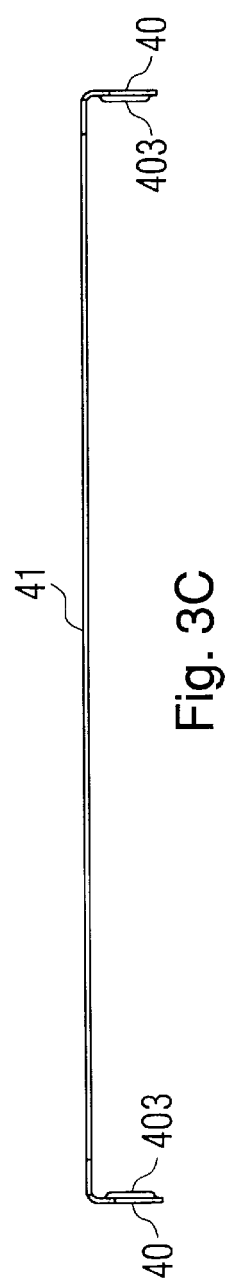

The lid 11 is shown in FIG. 1 and FIGS. 3A–3C. The lid includes a substantially planar portion 41, two ends 42, two side edges 43, and may also include downwardly-depending end panels 40. The term substantially planar is intended to include designs which are not perfectly flat or which include ribs, upwardly or downwardly extending portions. A preferred configuration of an end panel 40 includes a wide panel portion 401, a narrow panel portion 402, and an embossed recess 403 to facilitate handling of the lid. As seen in FIG. 3B, the narrow panel portion 402 is narrower than wide panel portion 401 by an amount X on each side. The shape of the lid corresponds to the case opening and has four corners 45a–d. At each corner of the lid corresponding to a corner of the case which is provided with a stud, the lid may have either a keyway 60 or a cutout 65. Each keyway comprises a small opening portion 61 and a large opening portion 62. Preferably, the contours of the keyway are smooth curves as seen in FIG. 3A, although the contours could also take other shapes such as one having sharp corners. Each keyway 60 has a keyway axis K—K which is substantially perpendicular to the longitudinal axis L—L of the case when the lid is aligned with the case as in FIG. 1. The cutouts 65 are not in the form of closed holes in the lid (as the keyways are), but are rather are topographically open shape features provided at the corners of the lids. If desired, these cutouts can instead be configured in the form of slots which would receive the stud members. These slots would be in addition to the longitudinal slots 50. As best seen in FIG. 1, the longitudinal slots 50 are arranged to accept the link arms of the handles when the handles are rotated to certain of the lid-securing positions.

In order for the keyways and studs to interact properly and contribute to securing the lid to the case, it is important that the diameter of the small opening portion 61 be greater than that of the shaft 21 but less than the diameter of the head 22, and that the diameter of the large opening portion 62 be greater than the widths of both the small opening portion 61 and of the head 22. In this way, when the lid is secured to the case, the areas of the lid surrounding the small opening portion will be encircling the shaft of the stud, and will be underlying the portions of the head of the stud which extend beyond the shaft. In this way, any potential movement of the lid upwards away from the top of the case the bottom surface will be prevented by the lid coming into contact with the bottom of the head.

For securement of the lid to the case, it is sufficient to provide only one keyway and one cutout portion on opposed portions of the lid. This would prevent disengagement of the lid when the handles are in the open position. These opposed portions of the lid are positioned perpendicular to the opposed positions of the handles to prevent movement of the lid in any direction.

The structure of the rotatable handles 16 and 18 may be understood by reference to FIGS. 1, 2, 4, and 5. The handles are provided for grasping, lifting, and carrying the surgical tray system 10. In a preferred embodiment, each handle is a wire bail handle formed from a single length of metal stock which is bent in the desired shape. In this embodiment, the metal stock is bent and shaped to have axle portions 163, a hand-grip portion 162, and link arm portions 161 linking the axle portions to the hand-grip portion. The axle portions are rotatably accepted by handle hubs 70 provided on the inner surface of each end wall, the combination of the axle portions and the hubs forming a rotational hinge allowing selected rotation of the handles. A guard plate 72 may be provided on each hub, in a plane offset from the end wall. The guard plate protects the hinge mechanism and also limits downward rotation by the handle.

The hinge has a rotation axis R—R defined by the longitudinal axis of the axle portions. This rotation axis is preferably perpendicular to the longitudinal axis L—L of the case. The hand-grip portion 162 is wide enough to allow a full hand hold by the user, and is preferably parallel with the rotation axis. The link arm portions 161 should be long enough to allow a clearance between the fingers and knuckles of the user and the tray system when a full hand hold is applied to the hand-grip portion, thus facilitating use of the handle to grip, lift, and carry the tray system.

It will be understood from reference to the figures that the axle portions 163 are formed by at least a part of the two end portions of the length of metal stock, the hand-grip portion 162 is formed by a central portion of the length of metal stock, and the link arm portions 161 are formed by the two portions of the length of metal stock intermediate the central and end portions. The axle portions 163 are parallel and colinear with the rotation axis for the handle.

In another preferred embodiment, the handles may be formed from two separate lengths of metal stock of circular cross section which are joined together. In this embodiment, the first length of metal stock forms an axle element for the handle, and the second length of metal stock is bent to form a gripping element for the handle. Specifically, the second length of metal stock is bent such that the central portion of its length forms the hand-grip portion, and the intermediate portions form the link arms. The gripping element can then be joined to the axle element by connecting the end portions of the second length of metal stock to the axle element, by welding, brazing, or other suitable means, to form the handle.

Figure 5:
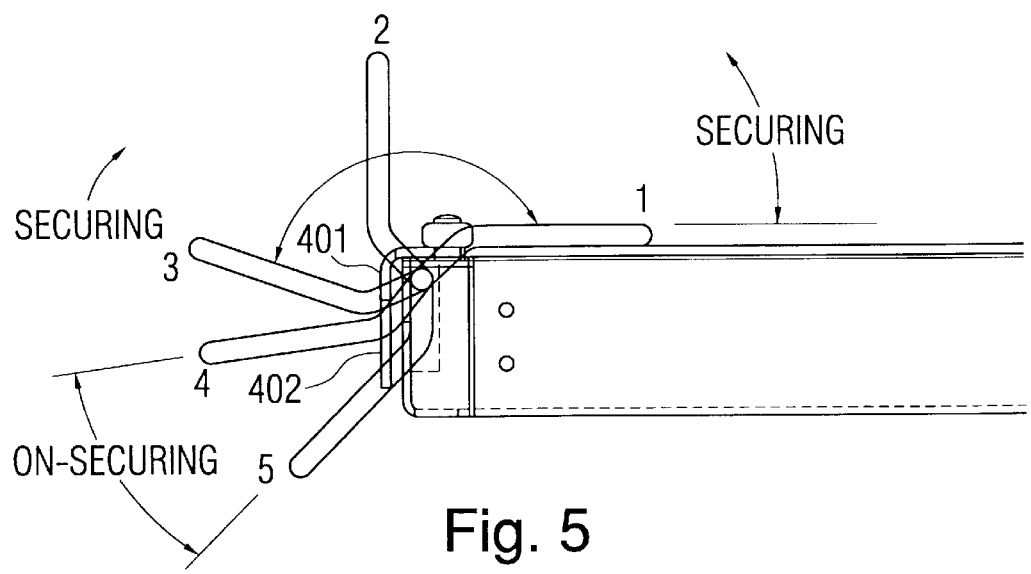
FIG. 5 is a partial side elevation view of the system illustrated in FIG. 1 showing a handle rotated to various positions.

The handles are free to rotate to a variety of angles, representing a variety of lid-securing and non-lid-securing positions, as shown in FIG. 5. In the fully closed lid-securing position 1, the handle is rotated fully upwards (i.e., clockwise in FIG. 5) until it comes to rest on, and further rotation is prevented by, the top surface of the cover. In the fully open non-lid-securing position 5, the handle is rotated fully downwards (i.e., counter-clockwise in FIG. 5) until the link arm comes into contact with, and further rotation is prevented by, the guard plate 72. If no guard plate is provided, handle rotation will be limited by contact of the link arms with the bottoms of the notches 310 in the end wall of the case, possibly resulting in undesirable marring of the notches by the handles.

When the handle is in fully closed lid-securing position 1 or an intermediate lid-securing position (represented for example by positions 2 and 3 in FIG. 5), the link arms are mechanically associated with some part of the lid, preventing any movement of the lid relative to the case in the direction transverse to the longitudinal axis. For example, in lid-securing position 1 the link arm is fully associated with the slot 50 in the planar portion of the lid, in lid-securing position 2 the link arm is partially associated with the slot and is also partially associated with the side of the wide panel portion 401, and in lid-securing position 3 the link arm is associated only with the side of the panel portion. Because the hand-grip portion of the handle lies on top of the lid when the handle is in the fully closed lid-securing position, it is accessible even when the tray system is in a confined physical enclosure which can only be reached from above (for example, when the tray is in a narrow sterilization enclosure which does not allow a user to reach their hands in between the outer sides of the tray and the inner sides of the enclosure).

Only when the handle is in an open or non-lid-securing position such as position 4 (an intermediate non-lid-securing position) or 5 (the fully open non-lid-securing position) are the link arms of the handle completely disassociated from the lid, thus allowing transverse movement of the lid. Such transverse motion effects a change in the relative position of the keyways and cutouts from the studs, allowing them to be disengaged from each other.

Because the narrow panel portion 402 of the end panel is narrower than the wide panel portion 401 by an amount X on both sides, the lid may be moved transversely at most a distance X, and no further, when the handle is in a non-lid-securing position. This distance X is selected to permit adequate relative movement of the lid to the case so as to permit the proper engagement and disengagement of the keyways and studs. It is important to prevent overshooting of the position which allows the proper engagement and disengagement of the keyways and studs. It will be understood that if, during a disengagement process, for example, the lid is slid too far (for example, until the shaft contacts the end of the large opening portion 62), the large opening portion will not be properly aligned with the stud to allow the lid to be lifted smoothly away from the case. Rather, part of the head of the stud will overly part of the lid and interference between the head of the stud and that part of the lid will prevent the lid from smoothly being lifted off the case directly upwards. The position which allows proper engagement and disengagement of the keyways and studs may be described as the position in which the shaft of the stud is located within, and preferably also centered within, the large opening portion 62.

Thus, the distance X established by the relative widths of the narrow and wide panel portions is selected such that the shaft of the studs are centered in the keyway precisely when the edge of the narrow panel portion comes into contact with the link arms of the handle when the lid is slid relative to the case in a direction transverse to the longitudinal axis of the case. In other words, the combination of the edge of the narrow panel portion 402 with a link arm 161 forms a stop which limits movement of the lid transversely relative to the case, such that the lid cannot overshoot the position relative to the case in which the keyways can properly disengage from the stud, allowing the lid to be lifted away from the case directly upwards.

Figure 2:
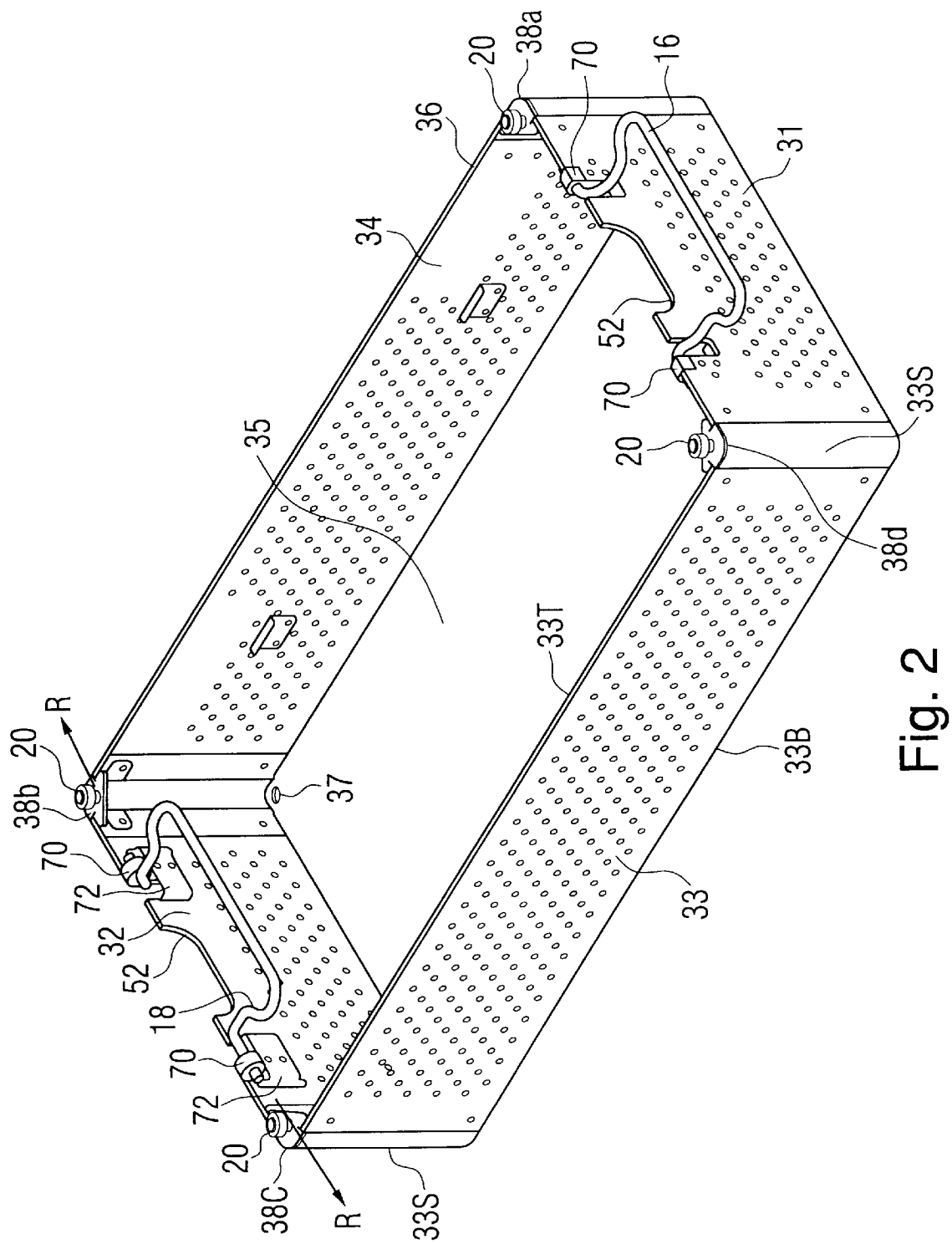
FIG. 2 is a perspective view of the case alone.

If the cases are to be stacked, the corners of base 35 of each case may be provided with through holes 39 (as seen in FIG. 2) or with recesses on the bottom surface of the base, near the corners of the base. The holes or recesses are positioned so as to mate with the tops of the heads of the studs of the case below when the cases are stacked, thus increasing the stability of the stacked tower of cases.

The method of use of the combined hand-hold and lid-securing system of the present invention will now be described. The case, as described above, and including the handles 16, 18 mounted in hubs 70 on the end walls, is placed on a work surface, and the handles are rotated downward until further motion is prevented by contact between the link arms and the guard plate 72 (see FIG. 5, handle position 5). When the case is ready to be covered, the lid is lowered onto the opening. Specifically, the lid is tilted about its longitudinal axis with the side edge having the cutouts 65 tilted downward. The cutouts 65 are then placed against the shafts of the studs at the corresponding opening corners, and the side edge of the lid having the keyways 60 is lowered down towards the lid opening. The cutouts are lid features which are topographically open with the periphery of the lid, as compared with the keyways which are closed holes fully surrounded by lid material. Accordingly, the initial positioning of the lid with the case is simplified by having two cutouts as compared to a system having keyways at all corners of the lid. The latter system would require relatively precise, painstaking positioning of the lid with the case.

As will be understood from FIG. 1, following the initial placement of the lid with the case, minor manipulation of the relative position of the lid and case transversely to the longitudinal axis of the case in the disengagement direction will be required to get the lid into the position such that large opening portions of the keyways are centered over the heads of the studs. The lid can then be completely lowered onto the case opening, and moved in the engagement direction until the shafts of the studs become located within, and come into contact with the end of, the small opening portions of the keyways and also come into contact with the sides of the cutouts. This is the engaged configuration of lid and case shown in FIG. 1; in this precise configuration, the engagement of the studs with the keyways and cutouts prevents the lid from being lifted away from the top of the case.

Of course, unless transverse movement of the lid back in the disengagement direction is prevented, the system is susceptible to a change in the relative position of the lid and case. When the handles are now rotated away from the non-lid-securing position to any lid-securing position, however, the association of the link arms of the handles with the lid will prevent any such transverse movement of the lid relative to the case. For example, when a handle is in the fully stowed lid-securing position, which is position 1 in FIG. 5 and the position of handle 18 in FIG. 1, the link arms are located in, and associated with, the longitudinal slots 50 in the planar portion 41 of the lid. In this lid-securing position, the association of the link arms with the sides of the slots prevents any significant transverse movement of the lid in the disengagement direction.

When the handles are used for lifting and carrying the case, they will be in one of the intermediate lid-securing positions, such as positions 2 and 3 of FIG. 5. The geometry of the handle shape, the hub placement, and the center of gravity of the case can be designed such that even when the system is lifted and suspended using just one handle, the link arms of the handle being used will be in an intermediate lid-securing position. Position 3 of FIG. 5 is representative of the position the handle would take if that handle alone were to be used to lift the case.

When it is desired to remove the lid, the system is placed on a work surface, and both handles are rotated to the open or non-lid-securing position, position 4 of FIG. 5. In this position, the link arms are no longer associated with any part of the lid, and the lid is now free to move in the disengagement direction. After a certain amount of such movement, the link arms and the sides of the narrow panel portions of the lid come into contact, preventing any further motion. In other words, the combination of the link arms and the narrow panel portions comprise a stop mechanism which limits the motion of the lid so that it will not overshoot the desired position for smooth disengagement of the keyways from the studs. The desired position is the one in which the shaft of the stud is located within, and preferably is centered in, the large opening portion of the keyway. In this position, when the lid is lifted directly upwards away from the case, the large opening portion of the keyways will pass smoothly past the heads of the studs.

The figures provided herein illustrate a particular embodiment of the system of the present invention in which there is a gap between the side edges of the walls of the case, which gap is bridged by upstanding corner brackets 13 which form the corners of the case. It will be appreciated by one of ordinary skill in the art, however, that the discussion of the structure of the case provided herein is not limited to the use of such brackets, and in fact the description above explicitly contemplates that the side edges of the walls of the case meet to form the corners of the case with no substantial gap between them. It will thus be appreciated by one of ordinary skill in the art that the details of the formation of the three-dimensional case from the four walls and the base is a routine matter of design choice, and that the invention is not limited to any particular technique used for formation of the case from the four walls and the base. It should also be understood that the above described embodiment of the present invention is merely one specific example adapted for a specific application in the field of surgical instrument cases. In addition, the configuration of the case is not critical to the invention, and round, oval or other polygonal shapes can be used if desired. The lid would conform to the opening of the case, and would be held in place by the handles, at least one keyway and one cutout or slot positioned such that movement of the lid is prevented in two perpendicular directions which are transverse to the longitudinal axis of the

What is claimed is:

1. A covered tray system comprising:
(a) a case comprising a base, at least one wall, and a longitudinal axis parallel to the wall, each wall extending from the base and having a top edge which forms an opening for the case;
(b) a pair of rotatable handles mounted to the wall, each handle having a rotation axis substantially perpendicular to the longitudinal axis, and a hand-grip portion, the handles being mounted in opposed relation and being rotatable, about the rotation axis, from a non-lid-securing position to a lid-securing position in which the hand-grip portion can be grasped using a full hand hold;
(c) first and second studs extending from the base toward the opening, with at least the first stud having a shaft and a head which is larger than the shaft;
(d) a lid for covering the case opening, the lid comprising a substantially planar portion having at least one keyway and at least one cutout, the keyway having a relatively smaller opening portion, a relatively larger opening portion, and a keyway axis substantially perpendicular to the longitudinal axis, the keyway being operatively associated with the first stud with the smaller opening portion of the keyway being larger than the shaft but smaller than the head of the first stud, and the larger opening of the keyway being larger than the head of the first stud, and the cutout being operatively associated with the second stud;

wherein movement of the lid in a direction transverse to the longitudinal axis is prevented when the handles are rotated to the lid-securing position, and the combination of the engagement of the at least one keyway with the first stud and the cutout with another stud results in a positive removable securement of the lid to the case, such that the lid cannot be removed until the handles are rotated to the non-lid-securing position, in which they are completely disassociated from the lid, and the lid is moved transversely relative to the case such that the at least one keyway can be disengaged from the first stud by lifting the lid away from the case and wherein each handle includes at least one link arm and the lid includes slots for receiving the link arms when the handles are rotated to the lid-securing position.

2. The system of claim 1 wherein the first and second studs are positioned in opposed relation on an axis that is perpendicular to a line extending between the opposed handles.

3. The system of claim 1 wherein at least two opposite side walls and two opposite end walls are included, each wall being joined to the base such that the top edges of the walls form a substantially rectangular opening, with the handles located on the end walls and the studs located adjacent the side walls.

4. The system of claim 1 wherein at least two first and two second studs are provided, with each stud having a shaft and a head which is larger than the shaft, and wherein the lid includes two keyways for engaging the first studs and two cutouts for engaging the second studs.

5. A tray system comprising:
(a) a substantially rectangular case comprising a base, a pair of opposite end walls, a pair of opposite side walls, and a longitudinal axis parallel to the side walls, each of the walls having two side edges, a bottom edge and a top edge, each wall being joined at its bottom edge to the base, the top edges of the walls forming a substantially rectangular opening having four corners;
(b) a rotatable handle mounted to each of the end walls, each handle having a rotation axis substantially perpendicular to the longitudinal axis, at least one link arm, and a hand-grip portion, the handle being rotatable, about the rotation axis, from a variety of non-lid-securing positions to a variety of lid-securing positions in which the hand-grip portion can be grasped using a full hand hold;
(c) at least one stud extending from the base, the stud located at one of the corners of the case opening, each stud having a shaft and a head, the head width being greater than the shaft width;
(d) a lid for covering the case opening, the lid comprising a substantially planar portion having two ends, two side edges, at least one keyway, and four corners corresponding to the corners of the case opening, each end being provided with one or more longitudinal slots arranged to accept the link arms of the handles when the handles are in certain of the lid-securing positions, each keyway located at one of the corners, each keyway having a relatively smaller opening portion, a relatively larger opening portion, and a keyway axis substantially perpendicular to the longitudinal axis, the width of the smaller opening portion being greater than the width of the shaft but less than the width of the head, and the width of the larger opening portion being greater than the width of the smaller opening portion and of the head;

wherein association of the link arms with the lid prevents relative movement of the lid and case in a direction transverse to the longitudinal axis when the handle is in any of the variety of lid-securing positions, and the combination of the engagement of the at least one keyway with the at least one stud and the association of the link arms with the lid results in a positive removable securement of the lid to the case, such that the lid cannot be removed until the handles are rotated to one of the variety of non-lid-securing positions, in which they are completely disassociated from the lid, and the lid is moved transversely relative to the case such that the at least one keyway can be disengaged from the at least one stud by lifting the lid away from the case.

6. The system of claim 5 wherein each handle comprises a wire bail handle formed from a single bent length of metal stock, the metal stock having a central portion, two end portions, and two intermediate portions connecting the central portion and the end portions, the metal stock shaped such that at least part of the end portions form axle portions disposed parallel to the rotation axis, at least part of the central portion forms the hand-grip portion, and at least part of the intermediate portions forming link arms interconnecting the axle portions and the hand-grip portion, the axle portions in combination with a hub member affixed to the case forming a hinge permitting the rotation of the handle.

7. The system of claim 5 wherein each handle comprises a wire bail handle formed from a plurality of initially separate lengths of metal stock including a first length of metal stock and a second length of metal stock, the first length of metal stock being substantially straight and forming an axle portion disposed substantially co-axially with the rotation axis;

the second length of metal stock having a central portion, two intermediate portions, and two end portions, and being shaped such that at least part of the central portion forms the hand-grip portion, and at least part of the intermediate portions form the link arms; wherein when the end portions of the second length of metal stock are connected to the first length of metal stock, the link arms interconnect the axle portion to the hand-grip portion, and the axle portion in combination with a hub member affixed to the case form a hinge permitting the rotation of the handle.

8. The system of claim 5 wherein when the lid is positively removably secured to the case and the system is carried by one handle, the link arms of the one handle will remain in a lid-securing position such that the link arms of the one handle are associated with the lid, thereby preventing transverse motion of the lid relative to the case and thereby also maintaining the positive removable securement of the lid to the case.

9. The system of claim 5 wherein the base is provided with holes or recesses such that when one case is stacked on top of another, the holes or recesses of the upper case mate with the studs of the lower case.

10. The system of claim 5 wherein the case is provided with four studs, one placed at each corner, each stud having a substantially cylindrical shaft and a substantially cylindrical head, the head diameter being greater than the shaft diameter.

11. The system of claim 10 wherein the lid is provided with two keyways, each placed at the corners at the ends of a first side edge, the corners at the ends of the other side edge being provided with cutouts which are topographically open.

12. The system of claim 10 wherein the lid is provided with a keyway corresponding to each stud on the case.

13. The system of claim 12 wherein the lid further comprises at least one downwardly-depending end panel located at the end of the lid, the end panel being substantially planar, parallel to the end walls of the case, and disposed outside the end wall of the case when the lid is secured to the case.

14. The system of claim 13 wherein the end panel and link arm in combination comprise a stop which allows the lid to be moved transversely relative to the case such that it will not overshoot the position at which the at least one keyway can be disengaged from the at least one stud by lifting the lid directly upwards away from the case.

15. The system of claim 13 wherein the end panel comprises a recess to facilitate handling of the lid.

16. A tray system comprising:
(a) a substantially rectangular case comprising a pair of opposite end walls, a pair of opposite side walls, a base, and a longitudinal axis parallel to the side walls, each of the walls having two side edges, a bottom edge and a top edge, each wall being joined at its bottom edge to the base, the top edges of the walls forming a substantially rectangular opening having four corners, a hub member provided on each end wall;
(b) a handle rotatably mounted to the hub member on each of the end walls, each handle comprising a wire bail handle formed from a single bent length of metal stock shaped such that at least part of the end portions of the length of metal stock is provided parallel to the rotation axis and at least part of the intermediate portion of the length of metal stock is shaped to provide the hand-grip portion, each handle having two link arms interconnecting the end portions and the intermediate portion, the end portions of the length of metal stock in combination with a hub member forming a hinge permitting the rotation of the handle, each handle having a variety of lid-securing positions in which the link arms are associated with some part of the lid and a variety of non-lid-securing positions in which the link arms are not associated with any part of the lid;
(c) four upwardly-projecting studs, each stud located at one of the corners of the case opening and having a substantially cylindrical shaft and a substantially cylindrical head, the diameter of the head being greater than that of the shaft;
(d) a lid for covering the case opening, the lid comprising:
a substantially planar portion having two ends, two side edges, and four corners corresponding to the corners of the case opening,
two longitudinal slots provided at each end, the slots arranged to accept the link arms of the handles when the handles are in certain of the lid-securing positions,
two keyways, each keyway located at one of the lid corners, each keyway placed at a corner at the end of a first side edge of the lid, each keyway having a small opening portion, a large opening portion, and a keyway axis substantially perpendicular to the longitudinal axis, the width of the small opening portion being greater than the width of the shaft but less than the width of the head, and the width of the large opening portion being greater than the width of the small opening portion and of the head;
two cutouts, each cutout located at the corner of the second side edge of the lid, each cutout being topographically open; and
a downwardly-depending end panel located at each end of the lid, the end panels being substantially planar, parallel to the end walls of the case, and disposed outside the end walls of the case when the lid is secured to the case, each end panel in combination with the link arms of the corresponding handle comprising a stop which allows the lid to be moved transversely relative to the case such that it will not overshoot the position at which the at least one keyway can be disengaged from the at least one stud by lifting the lid directly upwards away from the case;
whereby the association of the link arms with the lid prevents relative movement of the lid and case in a direction transverse to the longitudinal axis, and the combination of the engagement of the keyways and the cutouts with the at least one stud and the association of the link arms with the lid results in a positive removable securement of the lid to the case, such that the lid cannot be removed until the handles are rotated completely out of association with the lid and the lid is moved transversely relative to the case until further motion is prevented by the stop and the keyways and cutouts are disengaged from the studs, such that the lid can be lifted directly upwards away from the case.

17. The system of claim 16 wherein when the lid is positively removably secured to the case and the system is carried by one handle, the link arms of the handles will remain in one of the lid-securing positions, thereby preventing transverse motion of the lid relative to the case and thereby also maintaining the positive removable securement of the lid to the case.

* * * * *

UNITED STATES PATENT AND TRADEMARK OFFICE
CERTIFICATE OF CORRECTION

PATENT NO. : 6,116,452

DATED : September 12, 2000

INVENTOR : Hamel et al.

It is certified that error appears in the above-identified patent and that said Letters Patent is hereby corrected as shown below:

On the title page at "[73] Assignee": change "Synthes" to --Synthes (U.S.A.)--.

Signed and Sealed this

Twenty-fourth Day of April, 2001

*Attest:*

NICHOLAS P. GODICI

*Attesting Officer*  *Acting Director of the United States Patent and Trademark Office*